United States Patent [19]

Baharav

[11] Patent Number: 5,127,911
[45] Date of Patent: Jul. 7, 1992

[54] SANITARY FEMININE NAPKIN WITH A MECHANISM FOR OPTIONAL CONTOURING

[76] Inventor: Eva Baharav, 4190 Rd. 103, Carbondale, Colo. 81623

[21] Appl. No.: 345,178

[22] Filed: May 1, 1989

[30] Foreign Application Priority Data

May 3, 1988 [IL] Israel .......................... 86265

[51] Int. Cl.⁵ .............................. A61F 13/15
[52] U.S. Cl. ................... 604/385.1; 604/393; 604/402
[58] Field of Search ............ 604/385.1, 393, 402

[56] References Cited

U.S. PATENT DOCUMENTS

| 3,455,303 | 7/1969 | Wilson | 604/402 |
| 4,673,403 | 6/1987 | Lassen et al. | 604/385.1 |
| 4,781,713 | 11/1988 | Welch et al. | 604/385.1 |
| 4,828,555 | 5/1989 | Hermansson | 604/385.1 |

FOREIGN PATENT DOCUMENTS

0564905 11/1932 Fed. Rep. of Germany .

Primary Examiner—Randall L. Green
Assistant Examiner—Paul Prebilic

[57] ABSTRACT

A sanitary feminine napkin is provided, having a generally oblong shape and containing a fluid absorbent core interposed between a fluid impermeable backing and a fluid permeable cover, and a mechanism comprising a string means which allows a user the option of forming a contoured projection in the napkin, by pulling the string and drawing together part of the longitudinal edges of the napkin, therein rendering the napkin a labial napkin for enhanced adsorption of menses, and wherein placement of the mechanism allows the user various wearing options of the napkin in accordance with variations in menstrual flow and user activities during the menstrual cycle.

6 Claims, 6 Drawing Sheets

SANITARY FEMININE NAPKIN WITH A MECHANISM FOR OPTIONAL CONTOURING

BACKGROUND OF THE INVENTION

1. Field of the Invention

The present invention concerns a user-manipulatable mechanism which is to be attached to a feminine sanitary napkin to allow for an optional formation of a contour in said napkin, which contour is to be interposed between the labia majora in order to achieve a tighter fit between said napkin and the urogenital area so as to enhance efficient menstrual absorption of menstrual exudate.

2. Description of the Prior Art

Most, if not all, presently commercially used standard feminine sanitary napkins or pads comprise a multilayered flat pad construction, including at least a fluid absorbent core, a fluid permeable cover, and a fluid-impermeable backing. In addition, most, if not all, commercially-used pads have adhesive means to secure said pads to the undergarment of the wearer.

The class of feminine sanitary napkins is designed to possess three major attributes: (a) efficient absorbency, (b) a discreet design, and (c) comfort wear. However, as is well known to those skilled in the art, these attributes are extremely difficult to achieve within a given design of one and the same pad, as they are in mutual conflict: the more the desired absorbency attributes, the thicker the absorbing core, and, consequently, the less discreet and comfortable, and vice versa. It is therefore not too uncommon to find pads manufactured in a variety of thicknesses and shapes by leading commercial brands.

A number of approaches which have been proposed to solve this inherent attribute conflict in pad design has been within a class of napkins which will herein be called "contoured napkins"— a nomenclature loosely referring to napkins which depart from the flat construction described above. Indeed, contoured napkins have, in concept, two advantages: (a) they increase the absorbing core material while maintaining discreetness, as the extra material is positioned interlabially, and (b) they occlude menstrual exudate prior to egress and consequent forbidding staining. However, none of these approaches appear to be satisfactory for reasons which will be explained in the following brief review of a representative sample of approaches:

A number of pads have been suggested which comprise of two parts, either removable or built in. Thus, for example, U.S. Pat. Nos. 2,662,527, 3,183,909, 3,406,689, 3,528,422, and 4,079,739— all typically have a primary pad comprising absorbent material, and a secondary pad, usually of a lesser thickness and face area than the primary pad, to be inserted interlabially by the wearer and partly into the vestibule of said wearer. All of these pads are designed to achieve greater absorbence. However, they all suffer from one common disadvantage: uncomfortability. Their lack of comfort is due to their geometries which do not respect the urogenital female anatomy.

Another set of pads has been suggested characterized by a ridge-like construction to be interposed interlabially. U.S. Pat. Nos. 3,865,112, 3,983,873 and 4,046,147 are examples thereof. Since these geometries are uniform along the longitudinal axis, they are extremely irritable to the wearer over prolonged periods of time, as they press against either the clitoris or the buttocks of the wearer, or both, thus causing chafing and abrasion.

Another set of napkins, representative of which are U.S. Pat. Nos. 3,092,109 and 3,121,427, concerntrates on bypassing the uncomfortability of interlabial pad insertion by including a raised element at the distal end of the pad to be seated between the wearer's frenulum and rectum to effect a "damming" action deterring rearward leakage of menses— which is particularly effective when wearer is in supine position. A related napkin attending to the problem of rearward seepage is U.S. Pat. No. 4,536,181, which although rather different from the aforementioned napkins, features a shield which extends rearwardly to provide protection for the wearer during sleeping hours. However, inasmuch as these napkins attend to backward leakage they are much less effective with respect to forward seepage and leakage, in addition to being of questionable comfort to the wearer.

An approach which attempts to overcome these aforementioned problems is exemplifed in U.S. Pat. Nos. 4,631,062 and 4,673,403 where a labial pad is proposed with a raised profile in the posterior region of the pad intended for interposition within the vestibule of the wearer in order to achieve maximum occlusion of menstrual exudate while allegedly offering comfort due to its self-conforming attributes. While no explicit mention is made of how said pad is more self-conforming than any other contoured pad, a major disadvantage of U.S. Pat. No. 4,631,062 is the inability of the user to place the pad properly, a disadvantage acknowledged by the patentee who consequently coassigned a patent named "Method and Pad Allowing Improved Placement of Catamenial Device". This latter patent '403 provides "indicating means" for the proper placement of feminine pads. However, according to the patentee, even these means are not entirely "fool proof" and it is suggested that where there are women with anatomical differences, individualized and accurate placement can be achieved by inspecting the pattern of most staining in the previously used pad and making the proper adjustment in placement.

Review of the various appraches offered to solve these aforementioned problems reveals a consistent failure to acknowledge and address one maj/r parameter of the female menstrual cycle, namely, its intra-individual variability over and above inter-individual variability: Within one and the same menstrual cycle, there appears to occur variability not only with respect to heaviness of the menstrual flow, but also with respect to its direction as exemplified in Table 1 below, where staining patterns are shown as a function of day within the cycle, activity of the wearer, and other factors such as degree of tissue swelling.

TABLE 1

| portion of napkin | day in cycle: | | | | | |
|---|---|---|---|---|---|---|
| | 1st day | | 2nd day | | 3rd day | |
| dors. 7 | | | + | | | |
| 6 | | | ++ | + | + | |
| 5 | | | ++ | ++ | ++ | + | + |
| 4 | ++ | + | ++ | | + | ++ |

TABLE 1-continued

| portion of napkin | day in cycle: | | | | | | | | |
|---|---|---|---|---|---|---|---|---|---|
| | 1st day | | | 2nd day | | | 3rd day | | |
| 3 | ++ | + | | | ++ | | + | | |
| 2 | | ++ | | | ++ | | | | |
| ant. 1 | | ++ | | | + | | | | |
| activity: | SED | ACT | SUP | SED | ACT | SUP | SED | ACT | SUP |

Areas of menstrual staining on a feminine napkin as a function of activity (SED = sedentary, ACT = active, SUP = supine), and day in the menstrual cycle (1st, 2nd, and 3rd).
Abbreviations: dors. = dorsal end of napkin, ant. = anterior end of napkin, ++ = heavy staining, + = light staining Such immense variability calls for a flexible approach in pad design. As our research indicates, from a sample of 25 subjects, 19 women who preferred an experimental contoured pad during hours of heavy menstrual flow within the cycle, or for the night hours, when in supine position, also preferred a flat, non-contoured pad when their menstrual flow was lighter (three additional subjects preferred a contour throughout the whole menstrual cycle). Thus, inasmuch as an interlabial contour is less comfortable to the wearer than a flat pad, said wearer may prefer efficient absorbence of menses over comfort when her menstrual flow becomes lighter. Furthermore, and most importantly for those skilled in the art of feminine napkin design, the direction of menstrual seepage varies as mentioned above and exemplified in Table 1: some menstrual exudate tends to seep forward towards the clitoris and pubis, some seeps rearward, and some other seeps in the middle, opposite the vestibule, and soon leaks sideways toward the groin. These flow patterns furthermore depend on the condition of the swelling of the urogenital area during various periods throughout the menstrual cycle, on the type of activity in which the wearer engages, such as sports, sedentary, supine, etc., and on anatomical differences. All these factors affect the desired placement of the contoured pad for an effective occlusion of the menstrual exudate, which, in turn, calls for a variety of napkin designs to accommodate this large variability among napkin users.

Thus, there has yet to be devised a feminine napkin or pad, which offers featural flexibility to accommodate all the aforementioned requirements, while at the same time overcomes the disadvantages of lack of comfort and inefficient absorbence. The present invention fulfills that need.

SUMMARY

An object of this invention is to overcome the disadvantages of prior devices for absorption of menses. Another object of the invention is to provide a means for the optional contouring of flat commercially-used sanitary napkins, according to user's choice.

An additional object of the invention is to allow for different placement options of feminine napkins in position. An additional object of the invention is to achieve the aforementioned objects by minimal interference with the online production process of commercially-used feminine napkins.

These and other objects of the invention are accomplished by providing a mechanism, which is to be incorporated into a commercially-used sanitary feminine napkin during or after its manufacturing process. By "commercially-used sanitary feminine napkin" (hereafter abbreviated and referred to as napkin or pad) is meant a multilayered construction for absorbing menstrual fluids which has an oblong geometry containing at least a fluid absorbing core interposed between a backing of a fluid impermeable shield and a fluid permeable cover, which, in most instances, further includes adhesive means on its garment-contacting underside, which adhesive means is protected by a non-sticking shield or cover, prior to use. A napkin which contains a mechanism in accordance with the present invention will hereafter be designated as a "host pad". When incorporated into a napkin, said mechanism allows the user of said host pad the option of forming a contoured projection on the top, bodycontacting surface of said host pad when so desired. Thus with the incorporation of the mechanism in accordance with the present invention, any commercially-used napkin can become a multi-purpose convertible napkin determined by user's choice: under conditions of heavy menstrual flow, said host pad can be turned by the user into an interlabial pad, affording maximum flow occlusion of menses and enhanced absorption. When menstrual flow recedes, or when engaging in specific activities, said user can use said host pad in its standard flat manifestation, thus avoiding the unnecessary discomfort entailed in the interpostion of pad material within the labia majora.

The advantages of the present invention are realized in a user-manipulatable contour-shaping mechanism to be attached to a commercially-used flat napkin or pad during the manufacturing process of same. Said mechanism is so constructed that when unmanipulated, it does not alter the surface geometry of the host pad, neither does it interfere with its general shape. However, when manipulated in a specified manner, said mechanism forces all points prearranged to be in direct or indirect contact with the manipulating vector to be drawn together such that the host pad folds around said mechanism to form a sulcus on the underside of said host pad, which sulcus is a concavity of a projection formed on the top, body-contacting surface of said host pad. Most preferrably, said mechanism is to be located between the second and third sevenths of the longitudinal axis of the host pad either within the core material of the pad, or on its underside. When a user of said host pad chooses to obtain a contoured pad, she manipulates the said mechanism as directed. The contoured pad is to be disposed interlabially at a point where interruption of menstrual flow is most needed. The close contact between said projection and surrounding tissue is meant both to interrupt the menstrual flow and to enhance its absorption by the host pad. Preferably, the host pad should include extra absorbent core material around the edges adjacent to the herein proposed mechanism to make up for the amount of core material taken up by the said projection so that from top view, the generally oblong geometry of a standard commercially-used napkin is maintained when said host pad is in a contoured state. The proposed addition of core material will enhance the absorption capacity of the host pad in addition to providing a tighter, anatomically conforming fit.

It is further recommended that the addition of core material to the host pad extend with the plane of said pad so that from top view the host pad have a shoe-sole geometry when in a noncontoured state where one half of its length is oblong as are most commercially-used pads, and the other half of its length is rounded, having a transverse axis larger than the width of the oblong half. The shoe-sole geometry of said host pad provides the user with a large array of wearing options interrelating the flat versus the contoured manifestations of the host pad with frontal versus dorsal positioning of the said pad, to yield a highly versatile multi-purpose pad to fit a variety of anatomies, menstrual flow conditions, and activities. For example, when the menstrual flow is heavy, and the wearer of said host pad is engaged in a sedentary activity, she may prefer to wear said host pad in its contoured manifestation, with the rounded half anteriorly. When the menstrual flow is heavy, and said wearer is in a supine position, as for example during sleep at night, she may prefer to wear said host pad in its contoured manifestation as before, but with the rounded half dorsally, to protect herself from rearward leakage. When the menstrual flow is lighter, and said wearer is engaged in a physically more vigorous activity, such as walking or running, she may prefer a flat manifestation of the host pad, with an anterior placement of the rounded half of said host pad, in order to avoid possible chafing caused by the engagement of extra pad material with the buttocks, while at the same time adding extra pad protection anteriorly, where the menstrual flow may be directed when active physically. Lastly, when the menstrual flow is lighter, and said wearer is engaged in a sedentary activity, she may prefer to wear said host pad in its flat manifestation, with the rounded half dorsally where the direction of the menstraul flow is likely to reach when in that position and without an occluding projection inserted interlabially, as was the case exemplified earlier.

Other advantages of the present invention and a fuller appreciation of its manufacture and use, will be disclosed in the following detailed description of the preferred embodiments, taken in conjuction with the accompanying figures of drawing.

BRIEF DESCRIPTION OF THE DRAWINGS

FIG. 7b is a schematic longitudinal sectional view taken along the longitudinal axis of the host pad when contoured and in position as described in FIG. 7a.

DRAWING REFERENCE NUMERALS:

30 host pad
32 locus of mechanism
34 transverse edges
36 longitudinal edges
38 top surface
40 mechanism
42 adhesive strips
44 protective shield
46 bottom surface
48 string
50 longitudinal edges of mechanism
52 pulling tab
54 projection
56 elastic band
58 protective shield for 56

DESCRIPTION OF THE PREFERRED EMBODIMENTS

The present invention concerns a mechanism which mechanism is incorporated into a commercially-used sanitary napkin or pad in order to allow the user the formation of a contoured projection on the top, body-contacting side of said pad, so as to render it a labial feminine pad to be interposed within the labia majora of the user of said pad to attain a highly effective catamenial device.

The present invention will now be described with reference to certain preferred embodiments within the aforementioned contexts. However, it is to be realized that such descriptions are meant to be exemplary only, and should not be limitative of the scope of the present invention neither in mode of operation nor in construction.

Figure 1:
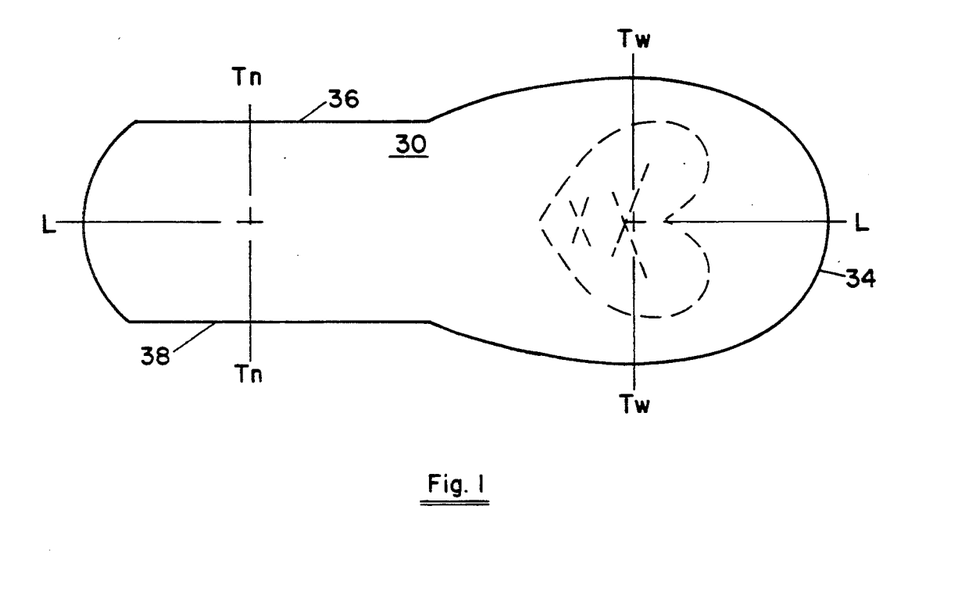
FIG. 1 is a top plan view of the host pad referred to in the present invention illustrating in phantom the preferred locus for the mechanism which is the subject of the present invention.
Figure 2:
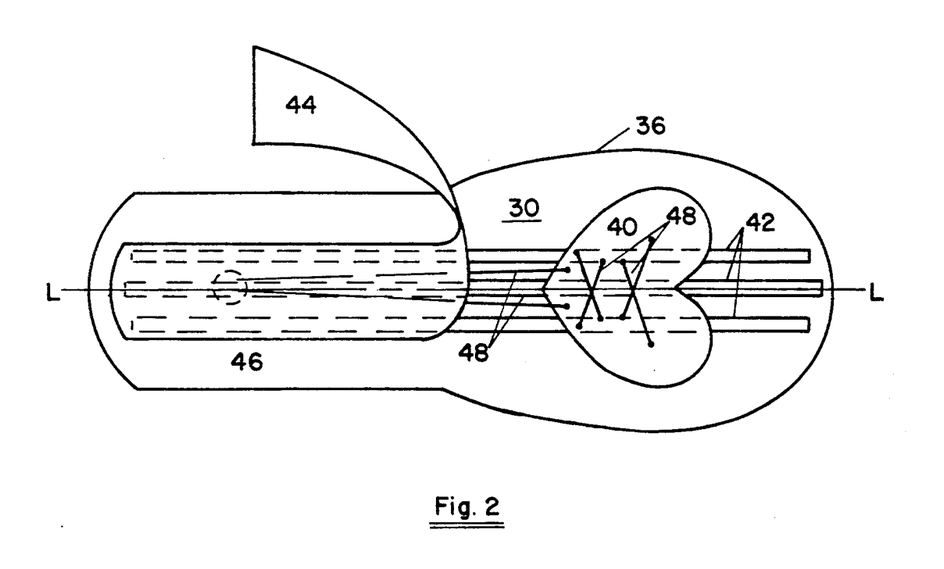
FIG. 2 is a bottom plan view of the host pad shown in FIG. 1 illustrating the layout of: (a) the mechanism of the present invention in respect to the host pad, (b) adhesive means for attaching the host pad to wearer's undergarment, and (c) a protective shield covering the adhesive means.

The mechanism in accordance with the present invention is incorporated into a commercially-used pad whose preferred design is illustrated in FIG. 1. A top plan view of the feminine pad, designated as 30, and hereafter referred to as the "host pad", indicates in phantom the preferred locus 32 of the mechanism in accordance with the present invention, which locus is most preferrably situated around the first quarter of the longitudinal axis "L" of the host pad 30. The preferred design for the host pad 30 is of a shoe-sole-like surface geometry extending between two transverse edges, 34, and two longitudinal edges, 36. The greater transverse axis, between the rounded portion of the edges 36, will be referred to as "Tw", and the smaller transverse axis, between the straight edges 36, will be referred to as "Tn". In one embodiment of the present invention, the mechanism, designated as 40, is attached to the underside surface, 46, of the host pad 30, as illustrated in FIG. 2. In the present description, unless otherwise specified, it is assumed that all commercially-used pads include adhesive means for attachment to the wearer's undergarment, usually in the form of one or several adhesive strips, designated as 42 in FIG. 2, covered by a protective shield, designated as 44 in same figure. This said adhesive means is used functionally with the operation of the mechanism as will be disclosed in the present description. Where no adhesive means is provided by the manufacturer of commercially-used pads, the mechanism 40 itself will include adhesive means as will be disclosed further in the present description.

Figure 3:
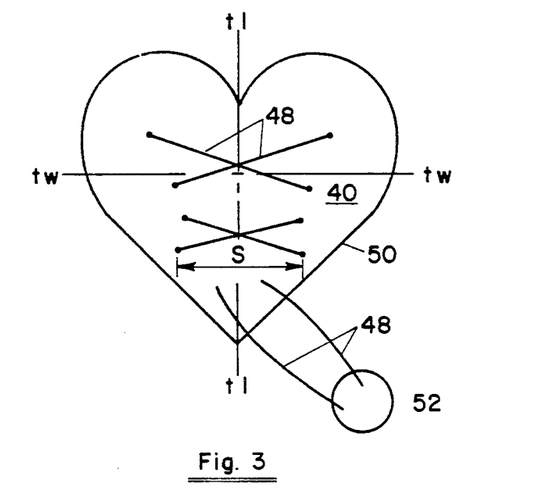
FIGS. 3 through 5 are top plan views of three possible embodiments of the mechanism in accordance with the present invention.
Figure 4:
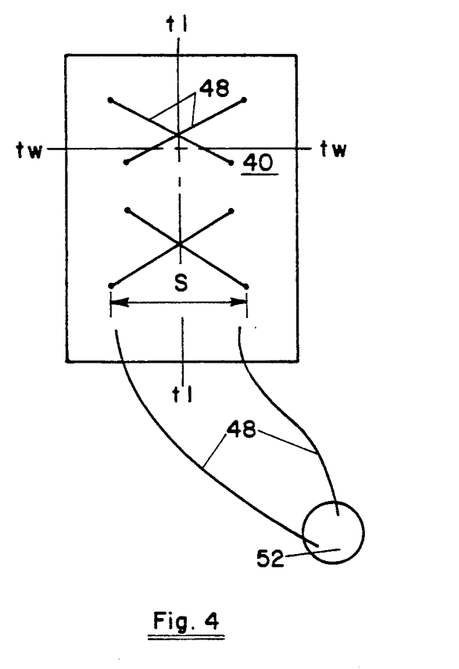
Figure 5:
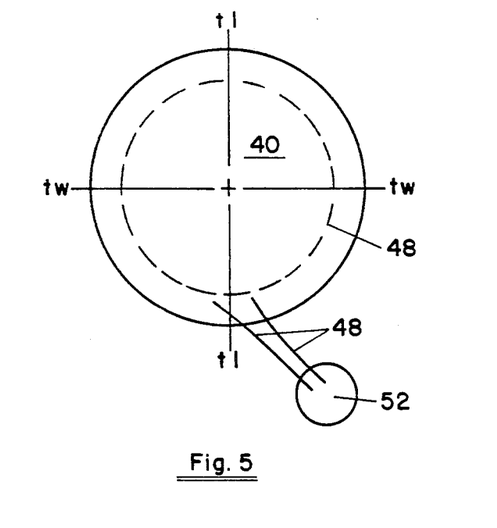

Three possible embodiments of the mechanism 40 in accordance with the present invention are illustrated in FIGS. 3, 4, and 5. In these embodiments, the mechanism 40 consists of a piece of soft, yet stiff, fabric, such as non-woven cloth, cut in some two-dimensional geometric shape with recommended dimensions as follows: A transverse axis "tw", measuring no less than half the size of Tn- the narrow transverse axis of the host pad 30, and no more than the size of Tw- the wide transverse axis of the host pad 30, and a longitudinal axis "tl" ranging between two sevenths and one third the length of the longitudinal axis L of the host pad 30. Furthermore, said piece of fabric includes a string, 48, preferably made of synthetic fiber, laced in a crisscross design through the fabric such that the string connects at least two pairs of two symmetrically opposed points along the longitudinal edges 50 of said fabric. It is further recommended that the minimum span, designated "S" in FIG. 3, between at least one pair of symmetrically opposed points connected by said string 48, should be third the size of the transverse axis Tw of the host pad 30. Furthermore, it is recommended that the lacing design span at least a seventh length of the longitudinal axis L of the host pad 30, and that the two free ends of said string 48 emerge from two symmetrically opposed points no further apart than third the size of Tn, close to the edge of the mechanism 40 which faces the center of pad 30. Said free ends of string 48 may emerge from either surface of said fabric. It is further proposed that some means be provided which ties the two string ends of string 48 together, which means is easily clasped by thumb and forefinger of user for easy manipulation. A means of this sort in the form of a tab, 52, is illustrated in FIGS. 3 through 5. FIG. 5 illustrates an embodiment of the mechanism 40 in the form of a fabric circle, where tw=tl=2r, and where the string 48 may be laced all around the peripherial edges of said circle, as an alternative to a criss-cross pattern.

Figure 6A:
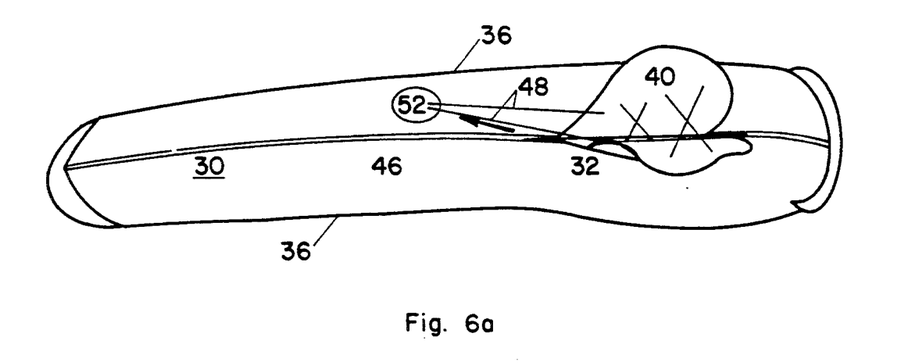
FIGS. 6a and 6b illustrate in perspective a two step operation of one embodiment of the mechanism in the present invention, with the bottom, garment-contacting surface of the host pad facing up.
Figure 6B:
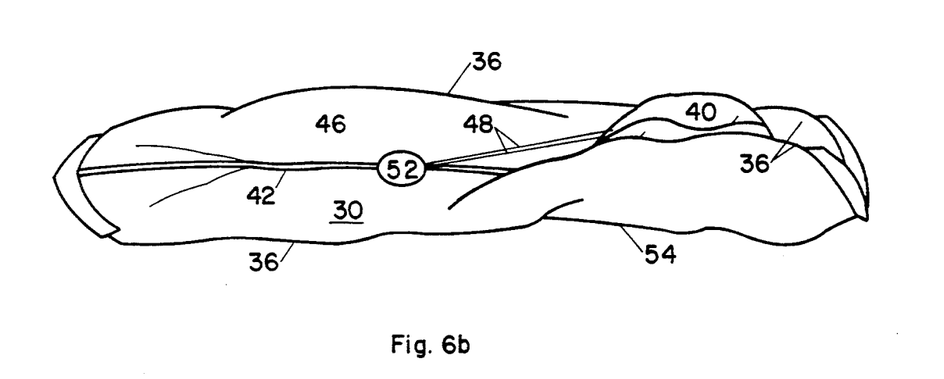
Figure 7A:
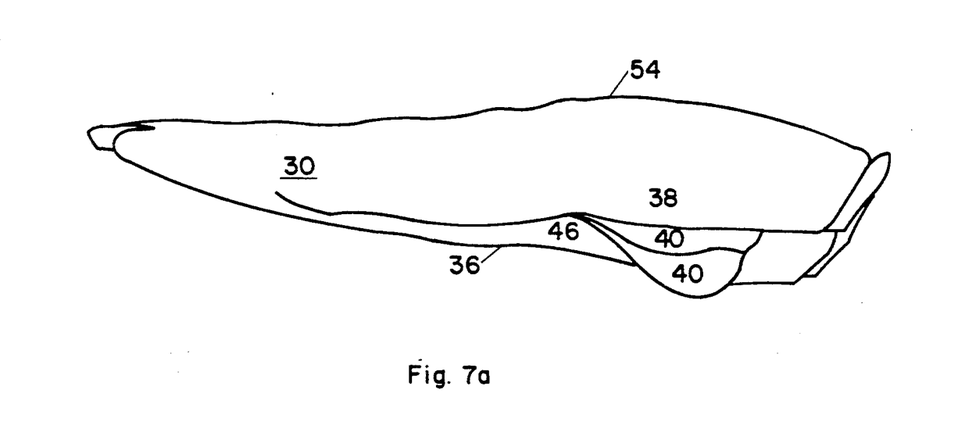
FIG. 7a illustrates a side view at an angle of approximately 25° of a contoured host pad resulting from the manipulation of the mechanism in accordance with the present invention, with the top, body-contacting surface of said pad facing up
Figure 7B:
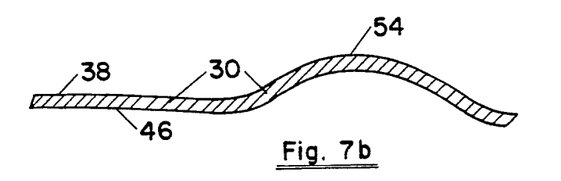

For purposes of exposition only, it is to be assumed that during the manufacturing process of the host pad the mechansim 40 is attached to the underside 46 of host pad 30, following the application of the adhesive means, 42, and that both adhesive means 42 and mechanism 40 are covered by protective shield 44. When the host pad 30 is to be used, the user holds said host pad with its bottom surface 46 facing up. After peeling the adhesive protecting shield 44, the host pad 30 is flat, and has on both sides of the mechanism 40 exposed adhesive 42 for the purpose of attaching the host pad 30 to the wearer's undergarment. The user who, at this point, has no need for a contoured pad, does not manipulate the mechanism 40, but turns the pad upside down, and positions the host pad 30 in place with its wider end anteriorly or dorsally, according to her choice depending on her activity, on menstrual flow conditions, and or on any other considerations as the case may be. If, however, the user is in need of a contoured pad, she uses the mechanism 40 in accordance with the present invention. FIGS. 6a and 6b illustrate a two step manipulation of the mechanism 40 for the attainment of a countoured pad: the user pulls the string 48 in the mechansim 40, by clasping the tab 52. It is illustrated how, as the string is being pulled, the longitudinal edges 36 of the host pad 30 are drawn towards each other, forming a sulcus in area 32 on the underside 46 of host pad 30, a convex of which sulcus is a projection, 54, formed on the top, body-contacting surface 38 of said host pad. At the final stage of the operation, as illustrated in FIG. 6b, the user presses the tab 52 against the adhesive means 42, in order to fix it in place so that it keeps the edges of the host pad 30 drawn together until the pad is turned upside down and positioned in place, within the labia majora. FIG. 7a illustrates a 25° tilted side view of a contoured pad resulting from manipulating the mechanism 40 in accordance with the present invention, and in FIG. 7b, a schematic longitudinal sectional view, taken along the longitudinal axis L of the host pad, illustrates the projection which forms on the top 38, body-contacting surface of the host pad.

When the order of applying the adhesive means 42 and the mechanism 40 during the manufacturing process of the host pad 30 is reversed such that said mechanism is applied to the host pad 30 first, by using some adhesive agent, and the adhesive means 42 is applied thereafter, said adhesive means will be superimposed on said mechanism which will have a functional consequence, as follows: The two longitudinal halves of the mechanism 40 will be forced towards each other when said mechanism is manipulated as explained before, and when the surfaces with the superimposed adhesive touch, they stick and cause the mechanism 40 to remain folded and ipso facto draw the surrounding edges 36 of the host pad 30 towards each other, creating the projection 54 as previously explained. This variation calls for a string 48 which is preferably wax-coated so as not to stick to the said adhesive material.

Figure 8:
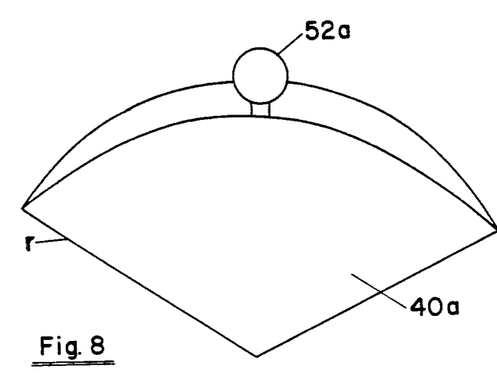
FIG. 8 is a schematic top view outline of another embodiment of the mechanism proposed in the present invention.
Figure 9:
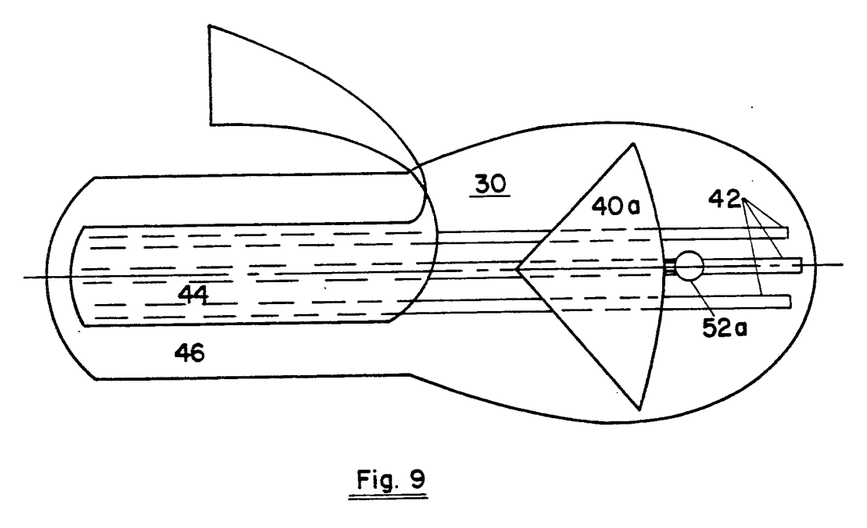
FIG. 9 is a bottom plan view of the host pad referred to in the present invention, with the mechanism illustrated in FIG. 8 attached to it.

FIG. 8 illustrates another embodiment of the mechanism 40 according to the present invention. In this instant, said mechanism consists of a cone-like construction, 40a, made of the same recommended fabric as before, namely of non-woven cloth. The cone-like construction 40a is folded in half along two radii equidistantly emanating from the vertex and flattened. It is proposed that the flattened angle of the vertex be approximately 120° and the length of the radius equal one seventh of the longitudinal axis L of the host pad 30. The flattened conical construction 40a can presently be envisioned as having two flaps, a top flap and a bottom flap, attached along the crease lines. It is the said bottom flap of mechanism 40a that is to be attached to the host pad 30, as illustrated in FIG. 9, with the longitudinal midlines of said host pad and said mechanism alligned, and with the vertex of mechanism 40a pointing towards the center point of said host pad. Thus the top flap remains loose and folded over the bottom flap.

Figure 10A:
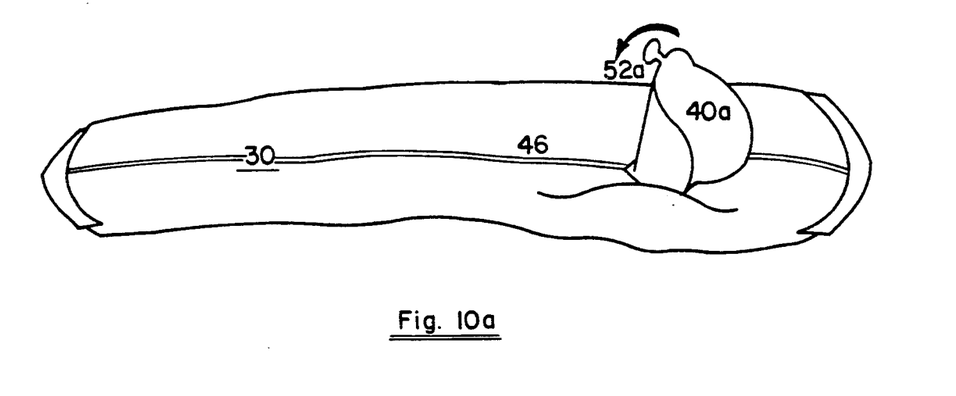
FIGS. 10a and 10b illustrate in two steps the operation of the mechanism illustrated in FIG. 8, with the bottom, garment-contacting surface of the host pad referred to in the present invention facing up.
Figure 10B:
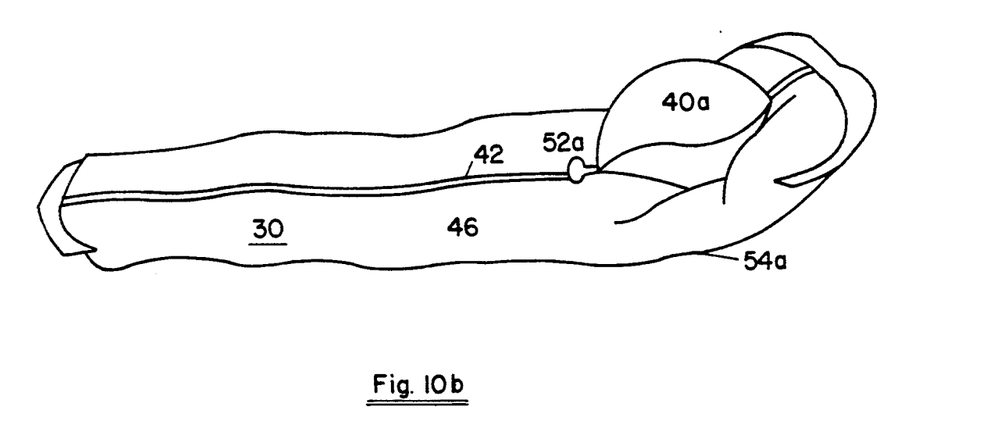

FIGS. 10a and 10b illustrate a two step operation of the mechanism 40a according to the present invention: the user in need of a contoured pad, holds the host pad 30 with its bottom surface 46 facing up and clasps a tab, 52a, which is attached to the top loose flap of mechanism 40a and bends it 180° towards the center of the host pad 30. This forces the cone-like construction open. The user then presses the tab 52a against the adhesive means 42, which fixes the cone-like mechanism 40a open in place, creating a crater-shaped sulcus on the bottom surface 46 of the host pad 30 which sulcus is a cone-like projection 54a on the body-contacting surface 38 of the host pad 30. The host pad 30 is now contoured and ready for insertion interlabially.

Figure 11:
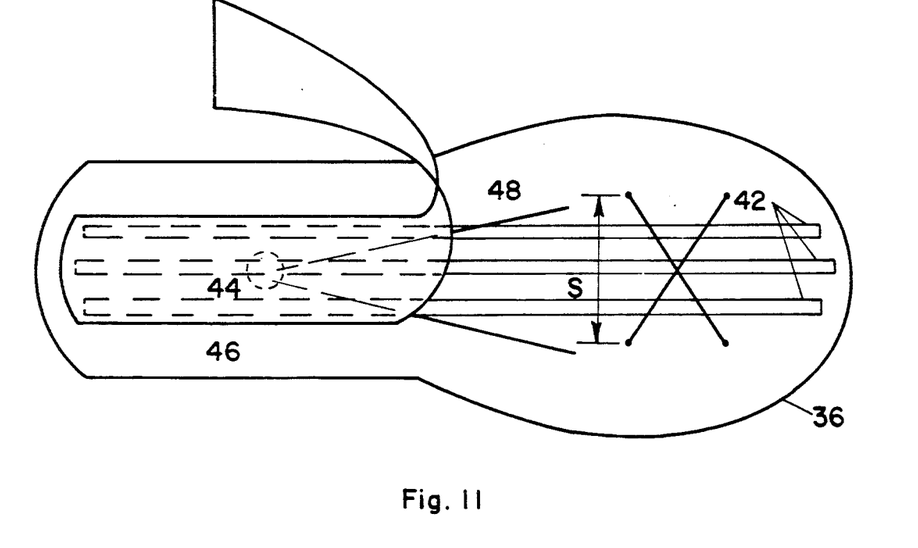
FIG. 11 is a bottom plan view of the host pad referred to in the present invention incorporating an embodiment of the mechanism of the present invention, with a threaded core.

Another embodiment of the mechanism 40 calls for lacing a string 48 through the host pad 30 itself as illustrated in FIG. 11. Said string is laced in either a crisscross or circle design through the core material of host pad 30. It is recommended that the same locus for the mechanism and the same proportions in the lacing design be kept as in the embodiments of the mechanism 40 illustrated in FIGS. 3 through 5.

In the presently discussed embodiment of the mechanism 40, the adhesive means 42 provided by the manufacturer of host pad 30, is functionally used with the present invention. That is to say, when the user chooses to manipulate the mechanism 40 in order to achieve a contoured pad, she pulls the string 48 by means of the pulling tab 52, and presses the tab 52 against the adhesive strips 42, fixing it thereon as exemplified in FIGS. 6a and 6b.

Although it is rare to find commercially-used feminine sanitary napkins without adhesive means for attachment to the undergarment of the wearer, and inasmuch as such adhesive means is functional with the operation of the mechanism which is the subject of the present invention, it is to be understood that the presence of such adhesive means is in no way a limitation on the scope and intention of the present invention. In the absence of such adhesive means on the host pad 30 the mechanism 40 will include, for example, a flat tab 52 which ties the string 48 ends together and which tab is coated by adhesive and covered by a protective shield. After creating a contour by pulling the string 48 all the way, the user peels off said protective shield and sticks the tab to the underside 46 of the host pad 30 at a point as far away from the mechanism as needed to leave the desired contour fixed in place. Optionally, the mechanism 40 itself may in addition be coated with adhesive means and covered by a protective shield. When the user chooses to manipulate the mechanism, she peels off the protecting shield so that the exposed adhesive surface when folded over itself, due to the operation of the mechanism as described herein, remains fixed and folded, forming the desired projection 54 as explained before.

Figure 12:
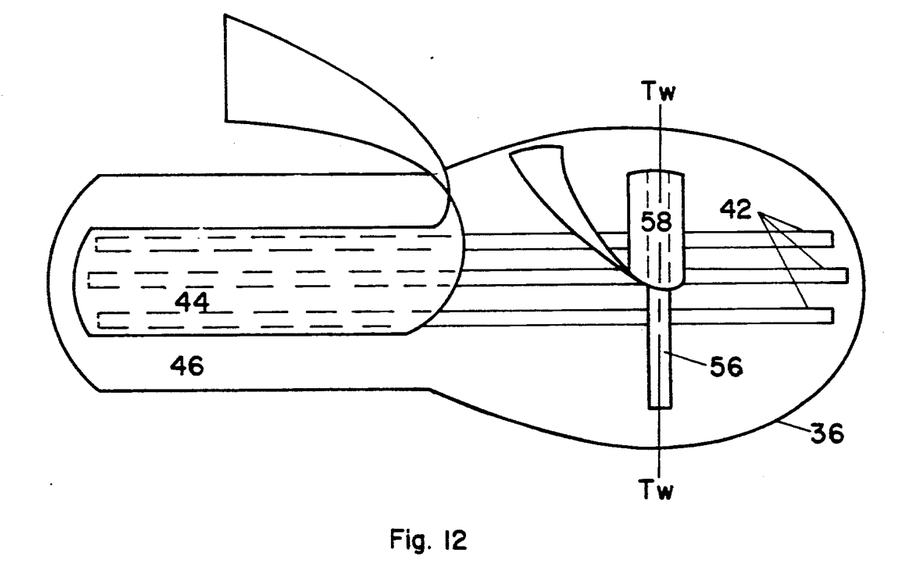
FIG. 12 is a bottom plan view of the host pad referred to in the present invention, incorporating an elastic band embodiment of the mechanism of the present invention, with part of its protecting shield peeled off.

Finally, another embodiment can be envisioned in accordance with the mechanism in the present invention where the drawing together of the longitudinal edges 36 of the host pad 30 around the area 32, is predesigned during the manufacturing process of host pad 30, but the pulling action is suspended pending the removal of a suspending element. This is achieved by providing elastic means on the underside cover 46 of the host pad 30, not unlike the means used commercially in most baby diapers for a tighter fit around the leg. This elastic means, in form of a band designated as 56 in FIG. 12, stretches along the transverse axis Tw of host pad 30, symmetrically on both sides of the longitudinal axis L of host pad 30 for no more than the length of Tn. During the manufacturing process of host pad 30, said elastic means is furthermore coated with adhesive, while in a stretched state, and covered with a protective shield, 58, which protective shield has two purposes:

(a) to keep the elastic band 56 stretched in a suspended state, and (b) to shield the adhesive which coats the elastic band 56 as explained.

Figure 13:
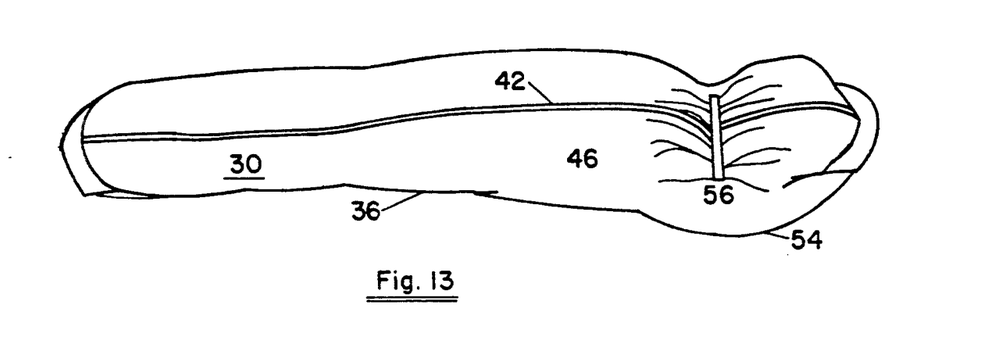
FIG. 13 illustrates in perspective the host pad referred to in FIG. 12 with its bottom, garment-contacting surface facing up and with the protecting shield completely removed. No adhesive means is illustrated.

When the host pad 30 is to be used as a contoured pad, the user peels off the protective shield 58, causing the elastic band 56 to contract and pull the edges 36 of host pad 30 on both sides of the elastic band 56 towards each other. As a result, a concave is formed on the bottom surface 46 of the host pad 30 and a convex projection 54 on the top, body-contacting surface 38 of said host pad, as illustrated in FIG. 13.

With this latter embodiment of the mechanism 40 on the host pad 30, the user has the same option of use and placement of pad as explained with the previously described embodiments of the mechanism 40.

The foregoing description exemplifies the wide range of styles which may be adapted in order to meet the functional objective of the present invention. The mechanism of the present invention is remarkable for the benefits it provides for the user of sanitary napkins. With the incorporation of the mechanism in accordance with the present invention, any commercially-used napkin can become a multi-purpose convertible napkin determined by user's choice: under conditions of heavy menstrual flow, said host pad can be turned by the user into an interlabial pad, affording maximum flow occlusion of menses and enhanced absorption. When menstrual flow recedes, or when engaging in specific activities, said user can use said host pad in its commercially-used flat manifestation, thus avoiding the unnecessary discomfort entailed in the interposition of pad material within the labia majora. Furthermore, the mechanism of the present invention is both simple in design and easy to incorporate into the on-line production process of commercially-used feminine sanitary napkins, which was one of the objects of the present invention. Indeed, as those skilled in the art will readily appreciate, there is a number of embodiments in which the mechanism of the present invention need simply be affixed to the surface of a napkin either before or after the application of adhesive means.

While the above description contains many specifications, the reader should not construe these as limitations on the scope of the invention, but merely as exemplifications of preferred embodiments thereof. Those skilled in the art will envision many other possible variations are within its scope. For example, skilled artisans will readily be able to change the dimensions and shapes of the various embodiments. They will also be able to make the mechanism of alternative materials, such as paper, woven cloth, or plastic. They can make variations on what type of manipulation the user is to exercise in order to achieve the desired contour in the host pad, e.g., they can use a combination of adhesive means plus mechanism as intended in the present invention where along both longitudinal sides of the adhesive strip there is a number of adhesive-coated flaps, which the user pinches together at points where a contour is desired. Accordingly, the reader is requested to determine the scope of the invention by the appended claims and their legal equivalents, and not by the examples which have been given.

I claim:

1. A sanitary feminine napkin having a generally oblong shape and containing a fluid absorbent core interposed between a fluid impermeable backing and a fluid permeable cover,
    said napkin further comprising a mechanism which allows a user the option of forming a contoured projection in said napkin,
    said mechanism comprising a string means, which, when pulled, draws together part of the longitudinal edges of said napkin and forms said contoured projection.

2. The napkin of claim 1 wherein said mechanism comprises a string laced in either a criss-cross or circular design through a piece of soft yet stiff material cut in some geometric shape with a longitudinal axis defined in relation to the longitudinal axis of said napkin, such that the ends of said string emerge at points one on each side of the longitudinal axis of said material in symmetrical fashion.

3. The napkin of claim 2 wherein said mechanism is attached by adhesion to the backing of said napkin within approximately the center of one half of the length of said napkin with longitudinal axes of said napkin and said mechanism aligned.

4. The napkin of claim 2 wherein said ends of string are tied by means of a tab, attachable by adhesion to the backing of said napkin.

5. The napkin of claim 1 wherein said mechanism comprises a string laced directly through said napkin within approximately the center of one half of the length of said napkin, in either a criss-cross or circular design, such that the ends of said string emerge from the backing of said napkin at points one on each side of the longitudinal axis of said napkin in symmetrical fashion.

6. The napkin of claim 5 wherein said ends of string are tied by means of a tab, attachable by adhesion to the backing of said napkin.

* * * * *